(12) United States Patent
Dirks et al.

(10) Patent No.: US 6,323,396 B1
(45) Date of Patent: Nov. 27, 2001

(54) AGROBACTERIUM-MEDIATED TRANSFORMATION OF PLANTS

(75) Inventors: Rob Dirks, Schiedam; Roger Peeters, Weert, both of (NL)

(73) Assignee: Nunhems Zaden BV, Haelen (NL)

( * ) Notice: Subject to any disclaimer, the term of this patent is extended or adjusted under 35 U.S.C. 154(b) by 0 days.

(21) Appl. No.: 09/512,650

(22) Filed: Feb. 24, 2000

Related U.S. Application Data

(63) Continuation of application No. PCT/EP98/05372, filed on Aug. 25, 1998.

(30) Foreign Application Priority Data

Aug. 25, 1997 (EP) .................................................. 97114654

(51) Int. Cl.[7] .............................. C12N 1/20; C12N 15/63; C12N 15/84
(52) U.S. Cl. ........................ 800/294; 800/298; 800/317.1; 800/307; 800/322; 800/317.4; 800/306; 800/320.1; 800/320.3; 800/320; 800/320.2; 435/469; 435/412; 435/411; 435/416; 435/419; 435/430; 435/421; 435/423; 435/424; 435/428; 435/430.1; 435/252.3; 514/1
(58) Field of Search ...................................... 800/294, 260, 800/298, 317.1, 307, 317.4, 322, 320.1, 306, 320.3, 320, 320.2; 435/469, 420, 421, 430, 431, 410, 252.2, 252.3, FOR 114, 117, 122, 192, 412, 411, 416, 419, 423, 428, 424, 430.1; 514/1

(56) References Cited

FOREIGN PATENT DOCUMENTS

| | | |
|---|---|---|
| 0116718B1 | 5/1990 | (EP) . |
| WO9113159 | 9/1991 | (WO) . |
| WO9534667 | 12/1995 | (WO) . |
| WO9712512 | 4/1997 | (WO) . |

OTHER PUBLICATIONS

Hiei, Y. et al., "Efficient transformation of rice (Oryza sativa L.) mediated by Agrobacterium and sequence analysis of the boundaries of the T–DNA." 1994, The Plant Journal, vol. 6, pp. 271–282.*

Sastry, G.R.K. et al., "Tryptophan Auxtrophs for Increasing Safety of Agrobacterium Ti–based Recombinant Plasmid Work." 1986, Plant Molecular Biology Reporter, vol. 4 (2), pp. 93–97.*

Komari, T. et al., "Methods of Genetic Transformation: Agrobacterium tumfaciens." 1999, Molecular Improvement of Cereal Crops, pp. 43–82.*

Swanson, E. B. et al., "Efficient isolation of microspores and the production of microspore–derived embryos from *Brassica napus*." 1987, Plant Cell Reports, vol. 6, pp. 94–97.*

Schmidt, R.M. et al., Phytopathology, vol. 59 (1969), pp. 1451–1454.

XP–002055372, Derwent abstract of JP47010999B.

Deblaere, R. et al., Methods of Enzymology, vol. 153 (1987), pp. 277–292.

Monacelli, B. et al., Protoplasma, vol. 142 (1988), pp. 156–163.

Lippincott, James A. et al., Jrnl. of Bacteriology, vol. 90, No. 4 (1965), pp. 1155–1156.

Lippincott, Barbara B.,et al Jrnl. of Bacteriology, vol. 92, No. 4 (1966), pp. 937–945.

Christen, Alice A., Z. Pflanzenphysiol. Bd., vol. 113 (1984), pp. 213–221.

Chang, Seok So et al., The Plant Journal, vol. 5, No. 4 (1994), pp. 551–558.

Bechtold, Nicole, Life Sciences, vol. 316 (1993), pp. 1194–1199.

Schmidt, R.M., et al, Phytopathology, vol. 59, No. 10, 1969, pp. 1451–1454.

Database WPI, Derwent Publications Ltd., London, GB; Class B05, AN 72–22820T.

* cited by examiner

*Primary Examiner*—David T. Fox
*Assistant Examiner*—Anne Kubelik
(74) *Attorney, Agent, or Firm*—Birch, Stewart, Kolasch & Birch, LLP

(57) ABSTRACT

Agrobacterium strains which have lost the capacity to proliferate vigorously in vitro or in planta, are provided, as well as transformation methods using these Agrobacterium strains.

19 Claims, No Drawings

SEQUENCE LISTING

<160> NUMBER OF SEQ ID NOS: 2

<210> SEQ ID NO 1
<211> LENGTH: 2345
<212> TYPE: DNA
<213> ORGANISM: Artificial Sequence
<220> FEATURE:
<223> OTHER INFORMATION: Description of Artificial Sequence: T-DNA of pGSV71
<221> NAME/KEY: misc_signal
<222> LOCATION: (1)..(25)
<223> OTHER INFORMATION: RB: T-DNA right border
<221> NAME/KEY: promoter
<222> LOCATION: (53)..(1436)
<223> OTHER INFORMATION: CaMV35S P3 promoter
<221> NAME/KEY: CDS
<222> LOCATION: (1437)..(1988)
<223> OTHER INFORMATION: region encoding phosphinotricin acetyltransferase
<221> NAME/KEY: 3'UTR
<222> LOCATION: (2007)..(2266)
<223> OTHER INFORMATION: 3' nos: 3' untranslated region containing the polyadenylation signal of the nopaline synthase gene of Agrobacterium T-DNA.
<221> NAME/KEY: misc_signal
<222> LOCATION: (2321)..(2345)
<223> OTHER INFORMATION: LB: T-DNA left border

<400> SEQUENCE: 1

```
aattacaacg gtatatatcc tgccagtact cggccgtcga ccgcggtacc cggaattcca    60
atcccaccaa aacctgaacc tagcagttca gttgctcctc tcagagacga atcgggtatt   120
caacaccctc ataccaacta ctacgtcgtg tataacggac ctcatgccgg tatatacgat   180
gactggggtt gtacaaaggc agcaacaaac ggtgttcccg gagttgcgca taagaagttt   240
gccactatta cagaggcaag agcagcagct gacgcgtata caacaagtca gcaaacagat   300
aggttgaact tcatccccaa aggagaagct caactcaagc ccaagagctt tgcgaaggcc   360
ctaacaagcc caccaaagca aaaagcccac tgctcacgct aggaaccaaa aggcccagca   420
```

-continued

```
gtgatccagc cccaaaagag atctcctttg ccccggagat tacaatggac gatttcctct    480
atctttacga tctaggaagg aagttcgaag gtgaaggtga cgacactatg ttcaccactg    540
ataatgagaa ggttagcctc ttcaatttca gaaagaatgc tgacccacag atggttagag    600
aggcctacgc agcaggtctc atcaagacga tctacccgag taacaatctc caggagatca    660
aataccttcc caagaaggtt aaagatgcag tcaaaagatt caggactaat tgcatcaaga    720
acacagagaa agacatattt ctcaagatca gaagtactat tccagtatgg acgattcaag    780
gcttgcttca taaccaagg caagtaatag agattggagt ctctaaaaag gtagttccta     840
ctgaatctaa ggccatgcat ggagtctaag attcaaatcg aggatctaac agaactcgcc    900
gtgaagactg gcgaacagtt catacagagt cttttacgac tcaatgacaa gaagaaaatc    960
ttcgtcaaca tggtggagca cgacactctg gtctactcca aaaatgtcaa agatacagtc   1020
tcagaagacc aaagggctat tgagactttt caacaaagga taatttcggg aaacctcctc   1080
ggattccatt gccagctat ctgtcacttc atcgaaagga cagtagaaaa ggaaggtggc    1140
tcctacaaat gccatcattg cgataaagga aaggctatca ttcaagatgc ctctgccgac   1200
agtggtccca aagatggacc cccacccacg aggagcatcg tggaaaaaga agacgttcca   1260
accacgtctt caaagcaagt ggattgatgt gacatctcca ctgacgtaag ggatgacgca   1320
caatcccact atccttcgca agacccttcc tctatataag gaagttcatt tcatttggag   1380
aggacacgct gaaatcacca gtctctctct ataaatctat ctctctctct ataacc atg   1439
                                                                Met
                                                                  1 gac cca gaa cga cgc ccg gcc gac atc cgc cgt gcc acc gag gcg gac   1487
Asp Pro Glu Arg Arg Pro Ala Asp Ile Arg Arg Ala Thr Glu Ala Asp
            5                  10                  15 atg ccg gcg gtc tgc acc atc gtc aac cac tac atc gag aca agc acg   1535
Met Pro Ala Val Cys Thr Ile Val Asn His Tyr Ile Glu Thr Ser Thr
         20                  25                  30 gtc aac ttc cgt acc gag ccg cag gaa ccg cag gag tgg acg gac gac   1583
Val Asn Phe Arg Thr Glu Pro Gln Glu Pro Gln Glu Trp Thr Asp Asp
     35                  40                  45 ctc gtc cgt ctg cgg gag cgc tat ccc tgg ctc gtc gcc gag gtg gac   1631
Leu Val Arg Leu Arg Glu Arg Tyr Pro Trp Leu Val Ala Glu Val Asp
 50                  55                  60                  65 ggc gag gtc gcc ggc atc gcc tac gcg ggc ccc tgg aag gca cgc aac   1679
Gly Glu Val Ala Gly Ile Ala Tyr Ala Gly Pro Trp Lys Ala Arg Asn
                 70                  75                  80 gcc tac gac tgg acg gcc gag tcg acc gtg tac gtc tcc ccc cgc cac   1727
Ala Tyr Asp Trp Thr Ala Glu Ser Thr Val Tyr Val Ser Pro Arg His
             85                  90                  95 cag cgg acg gga ctg ggc tcc acg ctc tac acc cac ctg ctg aag tcc   1775
Gln Arg Thr Gly Leu Gly Ser Thr Leu Tyr Thr His Leu Leu Lys Ser
        100                 105                 110 ctg gag gca cag ggc ttc aag agc gtg gtc gct gtc atc ggg ctg ccc   1823
Leu Glu Ala Gln Gly Phe Lys Ser Val Val Ala Val Ile Gly Leu Pro
    115                 120                 125 aac gac ccg agc gtg cgc atg cac gag gcg ctc gga tat gcc ccc cgc   1871
Asn Asp Pro Ser Val Arg Met His Glu Ala Leu Gly Tyr Ala Pro Arg
130                 135                 140                 145 ggc atg ctg cgg gcg gcc ggc ttc aag cac ggg aac tgg cat gac gtg   1919
Gly Met Leu Arg Ala Ala Gly Phe Lys His Gly Asn Trp His Asp Val
                150                 155                 160
```

-continued

```
ggt ttc tgg cag ctg gac ttc agc ctg ccg gta ccg ccc cgt ccg gtc        1967
Gly Phe Trp Gln Leu Asp Phe Ser Leu Pro Val Pro Pro Arg Pro Val
            165                 170                 175 ctg ccc gtc acc gag atc tga tctcacgcgt ctaggatccg aagcagatcg           2018
Leu Pro Val Thr Glu Ile
            180 ttcaaacatt tggcaataaa gtttcttaag attgaatcct gttgccggtc ttgcgatgat      2078 tatcatataa tttctgttga attacgttaa gcatgtaata attaacatgt aatgcatgac      2138 gttatttatg agatgggttt ttatgattag agtcccgcaa ttatacattt aatacgcgat      2198 agaaaacaaa atatagcgcg caaactagga taaattatcg cgcgcggtgt catctatgtt      2258 actagatcgg gaagatcctc tagagtcgac ctgcaggcat gcaagcttag atccatggag      2318 ccatttacaa ttgaatatat cctgccg                                          2345
```

<210> SEQ ID NO 2
<211> LENGTH: 183
<212> TYPE: PRT
<213> ORGANISM: Artificial Sequence
<220> FEATURE:
<223> OTHER INFORMATION: Description of Artificial Sequence: T-DNA of pGSV71

<400> SEQUENCE: 2

```
Met Asp Pro Glu Arg Arg Pro Ala Asp Ile Arg Arg Ala Thr Glu Ala
 1               5                  10                  15

Asp Met Pro Ala Val Cys Thr Ile Val Asn His Tyr Ile Glu Thr Ser
                20                  25                  30

Thr Val Asn Phe Arg Thr Glu Pro Gln Glu Pro Gln Glu Trp Thr Asp
            35                  40                  45

Asp Leu Val Arg Leu Arg Glu Arg Tyr Pro Trp Leu Val Ala Glu Val
        50                  55                  60

Asp Gly Glu Val Ala Gly Ile Ala Tyr Ala Gly Pro Trp Lys Ala Arg
 65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
        115                 120                 125

Pro Asn Asp Pro Ser Val Arg Met His Glu Ala Leu Gly Tyr Ala Pro
    130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                165                 170                 175

Val Leu Pro Val Thr Glu Ile
            180
```

AGROBACTERIUM-MEDIATED TRANSFORMATION OF PLANTS

This application is a continuation of PCT International Application No. PCT/EP98/05372 filed on Aug. 25, 1998, which designated the United States and on which priority is claimed under 35 U.S.C. § 120, the entire contents of which are hereby incorporated by reference.

This invention relates to the use of Agrobacterium strains which have lost the capacity to proliferate vigourously in vitro or in planta, particularly to the use of auxotrophic Agrobacterium strains, to generate transformed plants.

BACKGROUND OF THE INVENTION

Over the years many techniques for the genetic transformation of plants have been developed. These methods have as ultimate goal to obtain a transgenic plant, in which all cells contain a foreign DNA comprising a gene of interest (the so-called transgene) stably integrated in their genome, particularly their nuclear genome.

Different plant transformation methods have been described and can be classified into physical DNA delivery methods (e.g. electroporation, PEG-mediated DNA uptake, biolistics) or Agrobacterium-mediated DNA transfer. The latter one frequently is superior in efficiency, simplicity and quality of the transgenic plants (which generally comprise a smaller number of transgenes and have a lower occurence of aberrant transgenes).

Agrobacterium-mediated DNA transformation of plants is based on the capacity of certain Agrobacterium strains to introduce a part of their Ti-plasmid, i.e. the T-DNA, into plant cells and to integrate this T-DNA into the nuclear genome of the cells. It was found that the part of the Ti-plasmid that is transferred and integrated is delineated by specific DNA sequences, the so-called left and right T-DNA border sequences and that the natural T-DNA sequences between these border sequences can be replaced by foreign DNA (European Patent Publication "EP" 116718; 1987 Deblaere et al. (1 987) Meth. Enzymol. 153: 277–293).

Frequently, Agrobacterium-mediated transformation protocols call for the use of readily regenerable e excised plant tissues, organs or parts of organs, such as leaf discs, internodia, stem segments and the like. Alternatively, in vitro cultured tissues (e.g. compact embryogenic callus), suspension cultures or single cells (protoplasts) are employed as starting material to be transformed. For Arabidopsis, protocols have been described wherein seeds or total plants are inoculated (so called in planta transformation protocols).

A common feature of all protocols is that the cells, tissues or plants to be transformed are co-cultivated for a certain time with the Agrobacterium strains and subsequently, the proliferation of the Agrobacterium strains has to be restricted or eliminated by the use of bacteriocides or bacteriostatics such as antibiotics, particularly if further in vitro culturing is required. Frequently, the utilized concentrations of antibiotics interfere with or even inhibit the efficient regeneration of the transformed plant cells. Indeed it has been demonstrated that addition of certain antibiotics with a beta-lactam core structure, such as carbenicillin, to the plant medium may have cytokinin-like effects (WO 97/12512). Furthermore, the Agrobacterium strain of interest frequently comprises a bacterially expressed antibiotic resistance gene, such as but not limited to beta-lactamases, further restricting the spectrum of suitable antibiotics.

A problem frequently observed with the transformation of certain recalcitrant plant species, is that the regenerable cell layer may not be readily accessible to Agrobacterium-mediated transformation. Indeed, histogenetic analysis has demonstrated that e.g., in tomato, shoots induced by cytokinin treatment are derived from a few neocambial cells (Monacelli et al. 1988, *Protoplasma* 142, 156–163).

Another regularly encountered problem in Agrobacterium mediated transformation is the stress that vigourously proliferating Agrobacterium strains exercise on plants or plant parts, particularly when culturing the transformed plants or tissues in vitro, which may lead to inhibited regeneration or even death of the cells or explants.

Lippincott et al, 1965 (*Journal of Bacteriology* 90, 1155–1156) describe that auxotrophic mutants of Agrobacterium strain B6 are greatly reduced in infectivity (<1 to 30% of the parent specific infectivity).

Lippincot and Lippincott (1966, *Journal of Bacteriology* 92, 937–945) describe the further characterization of Agrobacterium mutant strains auxotrophic for adenine, methionine or asparagine and established that infectivity could be increased by simultaneously applying the required nutrient to the infected leaves at the time of infection with the auxotrophic Agrobacteria.

Christen et al. (1984, *Z. Pflanzenphysiol. Bd.*, 113 S. 213–221) demonstrated that leucine- and histidine requiring Agrobacterium tumefaciens mutants grow extremely poorly in the presence of dividing Nicotiana tabacum cv. xanthi protoplasts and suggested the use of such auxotrophic strains for cocultivation with plant protoplasts in the presence of a limiting amount of the required nutrient to allow temporary Agrobacterium division, as an alternative to the use of antibiotics.

Chang et al. (1994, *The Plant Journal* 5, 551–558) describe a transformation protocol for Arabidopsis involving severing of apical shoots at their bases, inoculation with Agrobacterium at the severed sites, and in planta generation of shoots from the severed sites to produce stably transformed progeny.

An improved in planta transformation method for Arabidopsis was described by Bechtold et al. (1993, *C.R. Acad. Sci. Paris, Sciences de la vie* 316: 1194–9) based on vacuum infiltration of a suspension of Agrobacterium cells into Arabidopsis plants, followed by selection of transformed progeny in the Ti seed. The authors assumed that a main limiting factor for the transformation frequency would be the restricted persistence of bacteria in the plant from the germination stage until the seed formation.

SUMMARY OF THE INVENTION

In accordance with the invention, provided is a process to produce a transgenic plant comprising a foreign DNA fragment integrated into the genome of at least some of its cells, comprising the following steps:

1) providing a plant or part of a plant, which is systemically infected with an auxotrophic Agrobacterium strain, preferably a methionine or cysteine requiring or a histidine and adenine requiring auxotrophic Agrobacterium strain, particularly LBA4404met or ATHVade, his, harbouring a DNA of interest which is linked to at least one T-DNA border sequence so as to be capable of being transferred to a plant cell, wherein the infected plant is preferably regenerated from explant tissue inoculated with said auxotrophic Agrobacterium strain; and 2) generating a transgenic plant from a single cell or a group of cells isolated from the systemically infected plant, preferably by in vitro regeneration of an explant tissue, a protoplast or a microspore isolated from the systemically infected plant or alternatively by germination of transformed progeny seed of the systemically infected plant.

The process may further comprise the step of applying the required nutrient to at least part of the systemically infected plant, preferably to the infloresence meristem or immature infloresence of the systemically infected plant, prior to the step of generating a transformed plant from the systemically infected plant.

Also provided by the invention are Agrobacterium strains auxotrophic for methionine or cysteine or auxotrophic for adenine and histidine, particularly LBA4404met or ATHVade,his, and their use in Agrobacterium-mediated transformation of plants, particularly in Agrobacterium mediated transformation of corn protoplasts, or alternatively in the Agrobacterium-mediated transformation of embryogenic callus, particularly embryogenic callus from cucumber or sugar beet.

DETAILED DESCRIPTION OF THE INVENTION

The present invention is based on the finding that auxotrophic Agrobacterium strains as hereinafter defined can survive when inoculated on an explant and succesfully establish a systemic infection of the regenerated plant. The presence of the endemic auxotrophic Agrobacteria does not interfere with the plant regeneration, even in the absence of bacteriocidal or bacteriostatic compounds. Moreover, such bacteria are still able to transform cells, as can be evidenced by the detection of transformed patches of marker gene expression in the regenerated plants. Finally, tissue explants from the systemically infected plants can be further cultivated in vitro, without bacteria overgrowing the explants.

The auxotrophic Agrobacterium strains of the invention allow controlled proliferation of the bacterial cells upon in planta and in vitro co-cultivation, and inoculated plants, tissues or cells are no longer overgrown by the proliferating bacteria. The Agrobacterium strains of the invention can thus be used to establish a plant systemically infected with such strains. The contacting time with the inoculated Agrobacterium strain is increased, allowing the bacteria to penetrate the inner plant tissues and reach and transform the appropriate target tissues such as the underlying regenerable cells. Such a prolonged incubation, however, can only be achieved if the vigorous proliferation of the bacteria can be controlled without killing them, as is achieved by the auxotrophic Agrobacterium strains of the invention. The method is particularly useful whenever an in vitro cultivation step is required in the generation of a systemically infected plant (e.g. regeneration of a systemically infected plant from a tissue explant, e.g. a stem segment).

Furthermore, the use of auxotrophic Agrobacterium strains to generate a plant systemically infected with such a strain and combination with the locally supplementing the required nutrient allows the local and controlled growth of Agrobacteria inside specifically targetted tissues, such as, but not limited to, the inflorescence yielding meristem.

Auxotrophic Agrobacterium strains suited for the methods of the invention, are those Agrobacterium strains which are unable to proliferate on a defined medium unless a particularly required nutrient (or nutrients) is (are) supplied to that medium. Preferably, the Agrobacterium strain is unable to proliferate vigorously in or on plant tissues.

Particularly preferred auxotrophic Agrobacterium strains are auxotrophic for molecules that are present only in limited amounts in plant tissues or intercellular fluids, more particularly for nucleosides or nucleotides (purine or pyrimidine) or amino-acids. Especially preferred is an Agrobacterium strain auxotrophic for an amino-acid, particularly auxotrophic for a sulfur-containing amino-acid, especially auxotrophic for cysteine or methionine. Especially preferred is an Agrobacterium strain, that produces a defective homocysteine methyltransferase (EC. 2.1.1.14) or no homocysteine methyttransferase at all. It is however known that mutations in other genes, such as the genes coding for homoserine succinyltransferase (EC 2.3.1.46), cystathonine (gamma)-synthase (EC 4.2.99.9) or cystathionine (beta)-lyase (EC 4.4.1.8), can also lead to an Agrobacterium strain auxotrophic for methionine and such strains can be used to similar effect.

Yet another especially preferred Agrobacterium strain is an auxotrophic Agrobacterium strain requiring two different nutrients, particularly requiring adenine and histidine, such as ATHVade,his.

It is preferred that the auxotrophic Agrobacterium mutant strain should have a low frequency of reversion. It is known in the art that deletion mutations result in a low frequency of reversion, and methods to generate deletions in bacteria are available to skilled artisan (e.g. Van Haute et al., 1983, *EMBO J.* 2: 411–417).

It goes without saying that all Agrobacterium strains, whether they belong to the species *rhizogenes, tumefaciens* or *radiobacter*, can be used according to the invention as host to harbour the T-DNA vectors and helper plasmids necessary to transfer the genes of interest to plant cells, provided they have a mutation rendering them auxotrophic as defined above. A prefered strain is an auxotrophic LBA4404 strain, particularly LBA4404met.

It should also be clear that the type of T-DNA vector or helper Ti-plasmid harboured by the auxotrophic host is not important for working the invention. It has been shown that certain Ti-plasmids such as the pTiBO542 derived pEHA101 (Hood et al. 1986 *J. Bacteriology* 168: 1291–1301) can improve the frequency of T-DNA transfer to plants. It has also been shown that introduction of the vir genes, particularly virG or virG together with virB, of a hypervirulent Ti-plasmid such as pTiBO542, on a replicon which is compatible with the resident Ti-helper plasmid, such as exemplified by pTOK47 (Jin et al., 1987 *J. Bacteriol.* 169, 4417–4425) can improve the frequency of T-DNA transfer to plants. It is clear that auxotrophic strains harbouring such plasmids can be used for the plant transformation methods of the invention. It has further been demonstrated that so-called superbinary vectors, comprising an extra virG gene of a supervirulent Ti-plasmid, particularly a virG gene from pTiBo542 can improve the frequency of transfer to certain plants (e.g. EP 0604662) and again auxotrophic strains harbouring such T-DNA vectors can be used for the plant transformation methods of the invention.

In accordance with this invention, a method is provided for producing a transgenic plant comprising a foreign DNA fragment integrated into the genome of at least some of its cells, comprising the following steps.

1) providing a plant or part of a plant, systemically infected with an auxotrophic Agrobacterium strain harbouring a DNA of interest which is operably linked to at least one T-DNA border sequence, preferably operably linked to two T-DNA border sequences; and 2) regenerating a transformed plant from transformed single cells or a group of transformed cells derived from the systemically infected plant.

In a preferred embodiment a systemically infected plant is generated by inoculation of an expiant tissue with an auxotrophic Agrobacterium strain, as herein described, harbouring a DNA of interest, followed by co-cultivation of the explant and the auxotrophic Agrobacterium strain in vitro for a period of time sufficient to establish a succesfully infection. Next, the excess of bacteria is removed and a systemically infected, intact plant is regenerated.

Methods to cultivate auxotrophic Agrobacteria are generally known in the art. It is thought to be important, in order to establish a succesfully systemic infection, that the required nutrients carried over from the cultivation medium are not completely removed prior to the inoculation step. Furthermore, an incubation of the auxotrophic Agrobacterium strain in the presence of plant phenolic compounds inducing vir-gene expression, such as e.g. acetosyringone, prior to inoculation, may be included in the methods of the invention. Such pre-induction with plant phenolic compounds has been amply described in the available literature (e.g. Vernade et al., 1988 *J. Bacteriol.* 170: 5822–5829). Alternatively, the vir-inducing compound may be supplied locally to the systemically infected plant.

The inoculation method used is expected not to be important. Preferably, the explant is submersed in a suspension of Agrobacterium cells with density or $OD_{600}$ ranging from 0.01 to 2, preferably from 0.1 to 1.5, particularly about 0.1. However, other methods such as vacuum infiltration, injection of Agrobacterium cells, and the like in plants or plant parts, can be used to the same effect.

It should be clear that it is not necessary that cells of the explant tissue are transformed, just that the explant is infected by the Agrobacterium strain, so as to be capable of regeneration into a plant which is systemically infected by the Agrobacterium strain.

It is thought that the main limitation for the explant tissue consists in the ability to regenerate into a whole plant, preferably into a fertile plant. Therefore, a wide range of explants, depending on the plant species to be transformed, can be used as starting material for the transformation methods of the invention, such as stem segments or internodia, callus tissues, preferably embryogenic callus, particularly compact embryogenic callus tissue of cereal plants.

In a preferred embodiment the co-cultivation of the explant and the Agrobacterium strain in vitro, extends for about two to five days, but is it thought that this time period can be shortened to as less as 1 day or extended to as much as 10 days. However, particularly with extended incubation periods, care has to be taken that the Agrobacteria, which continue dividing because of the residual required nutrients, carried over from the bacterial cultivation medium upon inoculation, do not completely overgrow the explant.

Excess of bacteria sticking to the surface of the explant, can optionally be removed e.g. Simply by washing or dipping on a sterile paper tissue.

Finally, a plant which is systemically infected with the Agrobacteria of interest, is regenerated, either in vitro, in soil or both. The method is particularly interesting where a regeneration in vitro is required, since the auxotrophic Agrobacteda cannot grow on unsupplemented, commonly used plant media (such as e.g. Murashige and Skoog medium) even in the absence of antibiotics.

Transformed plant cells may be enriched during the regeneration of the plant from the explant tissue, by cultivation on media containing a selective agent for the transformed plant cells as generally known in the art. For the method of the invention however it is important that the Agrobacteria can tolerate the used selective agent.

It is known that the auxotrophic Agrobacteria, which are present in the systemically infected regenerated plants, retain the capacity to transfer the DNA of interest to several tissues, and expression of a transgene has been demonstrated at least in anthers, leafs, flower primorida and the like. In view of the observed diversity of stably transformed tissue, it is thought that the Agrobacteria can gain access to all cells in all tissues, particularly to the regenerable cells and tissues.

The regenerated plants will normally consist of a mosaic of transformed and untransformed cells, and it is thought that different patches of transgenic cells may result from independent transformation events. In order to single out the different transformation events, a "clonal" step is preferably included in the process. By "cloning" is meant the process of regenerating a plant starting from single cells or a group of cells. A naturally occuring cloning process is provided by the gametogenesis. Haploid cloned plants can thus be generated e.g. by microspore culture. Homozygous plants with a limited number of transgene insertions can then be readily obtained as "doubled haploids". It is clear however that the gametes can be used to fertilize or be fertilized by a corresponding gamete to yield zygotic embryos.

Seeds, preferably seeds obtained through selfing of the regenerated plants, allow isolation of tranformed plant lines with a limited number of transgenes in the progeny of the regenerated plants systemically infected with the Agrobacterium strains. It is clear that not all progeny seeds necessarily will yield transgenic plants, but methods to detect the presence of transgenes (Southern, PCR, expression of marker genes) are well known in the art.

It should be appreciated that the above described cloning methods are only applicable to fertile plants. Plants which e.g. cannot undergo gametogenesis will require the use of in vitro cloning methods. Several methods are available in the art, including but not limited to protoplasting (e.g. described in Lijsebettens et al, 1986, *J. Mol. Biol.* 188, 129–145) mechanical disruption of the tissue (Meins and Binns, *Proc. Natl. Acad. Sci USA* 74, 2928–2932) or shoot generation from explants such as e.g. leaf discs. It is thought that the unability of the auxotrophic Agrobacteria strains present in the plant tissues to grow on the plant media used for in vitro culture, allowing the use of in vitro cloning systems without having to resort to bacteriocidal or bacteriostatic compounds, constitutes a major advantage of the described transformation processes.

Regenerated plants can be cured of the systemically spread Agrobacteria, by culturing the intact regenerated plants in the absence of the required nutrient and in the presence of a bacteriocidal compound, such as an antibiotic. It should be noticed that at this stage no regeneration is any longer required, hence the bacteriocidal compounds can be used despite their potential noxious effects on regeneration. It is also generally thought that Agrobacterium does not transmit via seeds. Harvesting progeny seeds thus represents an alternative way to obtain plants cured from Agrobacteria.

In accordance with this invention, transformation protocols are provided comprising the further step of stimulating locally the growth of the endemic Agrobacterium population, preferably at the site of appropriate target tissues, particularly at the site of inflorescence meristems. To this end, the regenerated plant, systemically infected by the auxotrophic Agrobacterium strain, is locally supplied with the required nutrient, particularly with the required methionine, to stimulate locally Agrobacterium division and transfer of the DNA of interest to the cells of the target tissue of interest. The mode of application is considered not to be important, and methods for application of chemicals to plants are generally available in the art (e.g. spraying with a solution of the required nutrient in 70% aceton).

In a preferred embodiment, the required nutrient is supplied to the cell lineage yielding the gametes and ultimately the seeds, particularly to the infloresence meristems or immature infloresences. In another embodiment the required nutrient is supplied to tissue particularly amenable for in vitro regeneration.

It is preferred to allow a time period, particularly at least one day, to lapse before proceeding to the cloning step. It is clear that in case infloresence meristems or immature infloresences have been supplied with the required nutrient, it is preferred that sufficient time is allowed to lapse to allow harvest of the gametes or the seeds.

It is clear that for the method of the invention, it is not strictly required that the whole plant be infected with the auxotrophic Agrobacteria. Plants wherein only parts, such as e.g. leaves, are infected by the auxotrophic Agrobacteria can be used as suitable material to isolate the transformed cells for regeneration of the transformed plants according to the method of the invention.

In this regard, it is important to note that a "systemically infected plant" as used herein, is a plant wherein the Agrobacterium strain is present in at least some part of the plant, preferably in at least several parts of the plants.

The described in planta transformation methods using auxotrophic Agrobacterium strains are expected to be suited for transformation of any plant for which regeneration methods from explant tissue are available. The methods of the invention will be especially suited for transformation of plants wherein the transformation and regeneration cannot be achieved in a single step. The in planta transformation methods are particularly suited for transformation of sweet pepper (*Capsicum annuum*) cucumber (*Cucumis sativus*), sunflower (*Heliantus annuum*), leek (*Allium ampeloprasum*), corn (*Zea mays*), wheat (Triticum spp, particularly *T. aestivum* and *T. turgidum*), barley (*Hordeum vulgare*), triticale (Triticosecale spp.) oat (Avena spp) rye (*Secale cereale*) and rice (*Oriza sativa*).

It is clear that the auxotrophic Agrobacterium strains of the invention can be used in any Agrobacterium-mediated plant transformation protocol, thereby obviating the need for control of the proliferation of the Agrobacterium with bacteriostatic or bacteriocidal compounds. It is believed that the auxotrophic Agrobacterium strains of the invention, preferably methionine requiring Agrobacterium strains, particularly LBA4404met are especially suited for use in transformation of plant protoplasts, particularly carrot petiole protoplasts, sugarbeet guard cell protoplasts, and corn protoplasts, and for use in transformation of callus tissue, preferably embryogenic callus tissue, particularly embryogenic callus tissue from sugarbeet or cucumber. The auxotrophic Agrobacterium strains of the invention are expected to be useful for the transformation all plants, either dicotylodonous or monocotyledonous but are particularly suited for the transformation of sweet pepper (*Capsicum annuum*) cucumber (*Cucumis sativus*), sunflower (*Heliantus annuum*), leek (*Allium ampeloprasum*), sugar beet (Beta spp), chicory (Cichorium spp.) corn (*Zea mays*), wheat (Triticum spp, particularly *T. aestivum* and *T. turgidum*), barley (*Hordeum vulgare*), triticale (Triticosecale spp.) oat (Avena spp) rye (*Secale cereale*) and rice (*Oriza sativa*)

Although not intending to limit the present invention to any one theory or mode of action, it is thought that the reduction in fitness of the auxotrophic bacteria in the used in vitro culture media is pivotal for the increased efficiency in transfer by reducing the stress induced by the vigorous proliferation and associated pathogenesis-related processes induced in the plant, yet avoiding the negative effects imposed on the plant cells, particularly protoplasts, of added bacteriostatic or bacteriocidal compounds.

The following Examples describe the methods of the invention in detail. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, N.Y. and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

In the examples and in the description of the invention, reference is made to the sequences of the Sequence Listing. The following free text is contained within the Sequence Listing:

<223> Description of Artificial Sequence:T-DNA of pGSV71

<223> RB: T-DNA right border

<223> CaMV35S P3 promoter

<223> region encoding phosphinotricin acetyltransferase

<223> 3'nos: 3' untranslated region containing the polyadenylation signal of the nopaline synthase gene of Agrobacterium T-DNA
<223> LB: T-DNA left border Strains LBA4404metHV and ATHVade,his have been deposited at the Belgian Coordinated Collections of Microorganisms (BCCM), Laboratorium voor Microbiologie—Bacterienverzameling (LMG), Universiteit Gent, K. L. Ledeganckstraat 35, B-9000 Gent, Belgium on Aug. 20, 1998, and have been attributed the following deposition numbers:

LBA4404metHV: LMG P-18486

ATHVade,his: LMG P-18485

EXAMPLES

Example 1

Selection of an Auxotrophic Agrobacterium Strain

A single colony from a freshly grown *Agrobacterium tumefaciens* strain LBA4404 (on LB medium supplemented with streptomycin 25 µg/ml) was inoculated in 5 ml of LB broth (supplemented with streptomycin 25 µg/ml) and grown at 28° C. on a rotatory shaker for 48 hrs. 2 ml of this culture was irradiated with X-rays at 600 Krad for 37.5 min or 200 Krad for 12,5 min. To 1 ml of the irradiated culture, 2 ml of minimal M9 medium (60 mM $K_2HPO_4$, 33 mM $KH_2PO_4$, 0.75 mM $(NH_4)_2SO_4$, 0.17 mM tri-sodium citrate.$2H_2O$, 0.02% $MgSO_4$, 0.2% glucose, 0.0005% thiamine) supplemented with 1 g/l Casamino acids and 25 µg/ml streptomycin were added, incubated for 48 hrs at 28° C. with shaking. These cultures were plated at appropriate dilutions and surviving colonies (about $10^6$ CFU/ml) were screened on minimal medium (25 µg/ml streptomycin) with and without 1 g/L Casamino acids. Two colonies were isolated which were unable to grow on unsupplemented minimal medium. These auxotrophic colonies were then used to inoculate a series of 2 ml liquid minimal M9 medium cultures supplemented with 0.1 mM of each of the amino acids separately and incubated at 28° C. with shaking for about 48 hrs. The first auxotrophic strain grew well on isoleucine and threonine supplemented media and grew slightly on asparagine, phenylaianine or alanine. The second auxotrophic mutant strain grew only on minimal media supplemented with methionine. This latter strain was designated LBA4404met.

LBA4404met was unable to grow on media comprising the direct precursor of methionin, homocystein. It can thus be deduced that the mutation in LBA4404met affects homocysteine methyltransferase.

Reversion mutation frequency was estimated by plating dense cultures of LBA4404met on minimal medium plates (not supplemented with methionine) and incubating for prolonged time at 28° C. Even after two weeks no colonies were observed on a plate inoculated with 10 µl of undiluted bacterial culture ($1.7 \times 10^8$ CFU/ml), allowing estimation of the reversion frequency as below $0.5 \times 10^{-7}$.

Example 2

Agrobacterium LBA4404met Mediated Transformation Efficiencies Improved by Inclusion of vir Genes Derived from a Hypervirulent Helper Ti-plasmid The nearly isogenic strains LBA4404met and LBA4404metHV comprising the T-DNA vector pNUN25 were used to evaluate the influence on the transformation efficiency of a hypervirulent helper Ti-plasmid in an auxotrophic Agrobacterium strain. Strain LBA4404metHV was obtained by introduction of plasmid pTOK47 (Jin et al., supra) in LBA4404met (by electroporation). pNUN25 is a T-DNA vector, comprising a nptII gene under control of a nos promoter and operably linked to a nos terminator between the T-DNA borders, as well as a bacterially expressed nptII gene outside of the T-DNA borders. It was constructed by introducing a DNA fragment comprising the glutamine-synthase coding region from *Nicotiana sylvestris* (having the sequence of the EMBL entry under Accession number X66940 from nucleotide 67 to nucleotide 1363) and to which an XbaI site (5' of the start codon) and an EcoRV site (3' of the end of the coding region) had been engineered by PCR amplification, into the XbaI/EcoICRI linearized pNUN5 (WO 94/29465).

*Nicotiana tabacum* leaf discs were incubated for two days in 5 ml MS20 medium [MS salts (Murashige and Skoog, 1968 *Physiol. Plant.* 15, 473–497) supplemented with 20 g/L sucrose] supplemented with 1 mg/L BAP (benzylaminopurine), and then inoculated with either LBA4404met(pNUN25) or LBA4404metHV(pNUN25) to a final $OD_{600}$ of 0.05. The co-cultivation was incubated at 27° C. for two days under a 16 hr/8 hr light/dark cycle. Next, the leaf discs were transferred to solidified MS20 medium supplemented with 1 mg/L BAP and 100 mg/L kanamycin. Kanamycin resistant shoots were removed as they emerged and further cultivated on selective medium. About 60 transformed shoots were isolated from about 100 leaf discs when LBA4404met(pNUN25) was used and about 223 transformed shoots were isolated from about 100 leaf discs when LBA4404metHV(pNUN25) was used.

This allowed to conclude that the vir genes of a hypervirulent Ti-plasmid still exerted the same effect in an auxotrophic background as observed in a prototrophic background by Jin et al. (supra).

Example 3

In Planta Transformation of Cucumber (*Cucumis sativa*)

Cucumber seeds of the genotype Gu1665-M were surface sterilized by incubation for 1 min in a 70% ethanol solution, followed by 15 min incubation in a 4% hypochlorite solution. The seeds were rinsed three times in sterile $H_2O$ and grown in vitro to plants. 24 internodia were harvested from the axenically grown cells and incubated for 30 min in 10 ml liquid MS20 to which LBA4404metHV (pNUN8) bacteria (grown in LB supplemented with 0.1 mM methionine, 100 mg/L kanamycin, 25 mg/L streptomycin and 2 mg/L tetracycline) were added to a final $OD_{600}$ of 0.1. pNUN8 is a T-DNA vector similar to pVDH99 (for description see below) wherein EcoRI/XhoI DNA fragment comprising the nptII chimeric marker gene has been replaced by a DNA fragment comprising the chimeric phosphinotricin acetyltransferase coding region between CaMV35S derived promoter and terminator sequences. The internodia were removed from the bacterial suspension and the excess of bacteria was removed by a quick blotting on filter paper. Next the inoculated internodia were transferred to MS20 solid medium for regeneration.

Healthy looking, regenerated plants were then used to demonstrate the presence of the bacteria in the flowers, as well as the presence of beta-glucuronidase activity in parts of the flowers by histochemical staining.

To demonstrate the presence of the Agrobacteria, 30 flowers from the gnotobiotically grown plants were each incubated in 1 ml of LB. In 28 cases bacterial growth was observed after 2–3 days of incubation.

Flowers were also histochemically stained for beta glucuronidase activity according to Jefferson(1987) (*Plant Mol. Biol. Rep.* 5(4): 387–405). In at least six flowers, blue spots indicating GUS activity and thus DNA-transfer in these tissues was observed. Pollen from flowers of these plants are used to pollinate female flowers. Seeds originating from the pollinated female flowers are germinated on phosphinotricin comprising media to obtain transformed plants.

Example 4

In Planta Transformation of Tobacco (*Nicotiana tabacum*)

Internodia were isolated from axenically grown tobacco plants (SR1) and incubated for 120 min in a suspension ($OD_{600}$ 0.05/in 30 ml MS20) of LBA4404metHV (pNUN8) bacteria. Next the internodia were transferred to a solid MS20 medium supplemented with 10 µM acetosyringone. Young leaves from in vitro regenerated plants were subjected to histochemical GUS-staining and blue sectors of different sizes were observed in several leaves. The difference in size of the stained sectors might reflect the entrance the time-point at which the T-DNA entered the precursor cell(s) in the cell lineage. Leafs of the regenerated plants are used as starting material to isolate leaf discs, which are cultivated on PPT-comprising media to obtain transgenic shoots and ultimately transgenic plants (according to the method described by Horsch et al., 1984, *Science* 223:496–498).

Example 5

In Planta Transformation of Tomato (*Lycopersium esculentum*)

Internodia were isolated from axenically grown tomato plants (Moneymaker) and incubated for 15 min in a suspension ($OD_{600}$ 0.05/in 30 ml MS20) of LBA4404metHV (pVDH99) bacteria. pVDH99 is a plasmid comprising a T-DNA with a 35S GUS-intron chimeric gene as described by Van Canneyt et al. (1990, *Mol. Gen. Genet.* 220: 245–250) and a chimeric selectable CaMV35S-nptII gene. The plasmid further comprises a bacterial kanamycin resistance. Next the internodia were transferred to a solid MS20 medium supplemented with 10 µM acetosyringone. Young leaves from in vitro regenerated plants were subjected to histochemical GUS-staining and blue sectors of different sizes were observed in several leaves. The difference in size of the stained sectors might reflect the entrance the time-point at which the T-DNA entered the precursor cell(s) in the cell lineage. Leafs of the regenerated plants are used as starting material to isolate leaf discs, which are cultivated on kanaycin-comprising media to obtain transgenic shoots and ultimately transgenic plants (according to the method described by Mc Cormick et al., 1986 *Plant Cell Reports* 5: 81–84).

Example 6

In Planta Transformation of Leek (*Allium ampeloprasum*)

For this purpose, fully mature field grown plants are used and harvested. Plants are left to dry for 3 days in order to reduce infections. Basal plates are collected, cut in four pieces (with complete elimination of the roots) and subsequently sterilized by submersion for 1 minute in 70% ethanol, followed by 20 minutes treatment with 2% NaOCl (commercial bleach). After this treatment the explants are washed 4 times with sterile water, with 10 min intervals between the washing steps.

These explants are transferred to induction medium [DS macro elements (Dunstan and Short, 1979, *Sci Hort* 112: 3743), MS microelements (Murashige and Skoog, 1968 see infra), FeEDTA, thiamine 10 mg/L, pyridoxine 1 mg/L, nicotinic acid 1 mg/L, inositol 100 mg/L, sucrose 30 g/L, isopentenyl adenine (2-IP) 4 mg/L NAA, NAA 1.25 mg/L, Agar 8 g/L]. After 3 to 4 weeks incubation at 21 ° C. with a light intensity of 2000 to 4000 lux, the first plantlets emerge, which are then used for the inoculation with Agrobacterium LBA4404metHV (pVDH99). To this end, the young plantlets are removed form the initial explants and an incision is made in the basal part of the young plantlets. This wounded basal part is soaked in an Agrobacterium suspension with an $OD_{600}$ of about 0.01 for a period of 30 minutes. The excess of Agrobacterium suspension is quickly removed by blotting on filter paper, prior to transfer to the induction medium. The inoculated plants develop adventitious plants, some of which are tested by histochemical GUS staining to verify the presence of putative transgenic sectors. Similar adventitious plantlets are transferred to a medium that allows the outgrowth to mature leek plants [similar to the induction medium except that NAA is reduced to 0.1 mg/L and sucrose to 20 g/L. Seeds are harvested from the regenerated mature plants and germinated to obtain transgenic plants. Transgenic plants are recognized by their ability to grow on kanamycin containing media. Transgenic plants are further recognized by PCR detection of the inserted T-DNA sequences.

Example 7

Agrobacterium Mediated Transformation of Embryogenic Callus from Cucumber (*Cucumis sativa*)

Embryogenic callus from cucumber genotype 941687-G was generated as described (Chee, P. (1990) *Hortscience* 25 (7), 792–793). The callus was cut in a petridish into little pieces of less than 1 mm in 5 ml MS30 2/0.5 2–4D/kin [MS salts (Murashige and Skoog, 1968 *Physiol. Plant.* 15, 473–497) supplemented with 30 g/L sucrose, 2 mg/L 2,4-dichlorophenoxy acetic acid (2,4-D) and 0.5 mg/L kinetin]. To this petridish, an *Agrobacterium tumefaciens* LBA4404metHV(pTOK47) (pVDH99) suspension was added to a final $OD_{600}$ of 0.5. The bacteria had been cultivated for 2 days at 28° C. with shaking, in 10 ml LB supplemented with 0.1 mM methionine, 100 mg/L kanamycin, 25 mg/L streptomycin and 2 mg/L tetracyclin. The bacteria were harvested by centrifugation, washed with the MS30 2/05 2–4D/kin medium and resuspended to the original density.

After 4 days of co-cultivation at 270° C. in the dark, the calli were washed twice with 25 ml of liquid MS30 2/0.5 medium, plated on solid medium MS30 2/0.5 supplemented with 100 mg/L kanamycin, and further incubated at 27° C. in the dark. After two weeks, selected calli were subjected to histochemical GUS-staining as described by Jefferson (1987) (*Plant Mol. Biol. Rep.* 5(4): 387405). Blue sectors could be visualized in at least 5 calli, indicative of cells transformed by the T-DNA of pVDH99. Healthy looking sectors of the calli grown on the selective medium were dissected out and transferred to similar medium without kanamycin, to allow regeneration.

Example 8

Transformation of Carrot Protoplasts by an Auxotrophic Agrobacterium Strain

Carrot protoplasts were isolated from Daucus carrota var Sytan B142 petioles according to Dirks et al., 1996 (R. Dirks, V. Sidorov, C. Tulmens 1996, *Theor. Appl. Genet.* 93: 809–815) resuspended at a density of $8 \times 10^5$ protoplasts ml in CPP-CA (CPP medium according to Dirks et al., 1996 with omission of the casamino acids) supplemented with 0.1 mg/L 2,4-D and 0.2 mg/L zeatin. Four petridishes containing 1.5 ml of protoplast suspension were co-cultivated with *Agrobacterium tumefaciens* LBA4404met (pNUN20) (added to a final $OD_{600}$ of 0.05) for two days at 27° C. No antibiotics were added to the protoplast culture media. The bacteria were harvested and washed prior to addition to the protoplasts, to remove the methionine.

pNUN20 is a T-DNA vector comprising a T-DNA with a chimeric selectable nptII gene and a chimeric gene consisting of a CaMV 35S promoter operably linked to a beta-subunit H+ ATPase (Shinozaki, K., Devo, H., Keto, A. and Suginec, M. (1983) *Gene* 24, 147–155; EMBL-database accesion number K00507) followed by a nopaline synthase gene terminator. The plasmid further comprises a bacterial kanamycin resistance gene outside of the T-DNA borders.

After two days, 1.5 ml of alginate was added to each petridish and the alginate discs containing the protoplasts were floated on 3 ml CPP-CA supplemented with 0.1 mg/L 2,4-D and 0.2 mg/L zeatin, for about 12 days before addition of 100 mg/L kanamycin. The discs were further incubated about two weeks. Next, the alginate discs were dissolved in 40 mM sodium citrate, washed, resuspended in 5 ml CPP-CA 30/20 S/N supplemented with 0.1 mg/L NAA (naphtalene acetic acid) and 0.2 mg/L zeatin and plated on solid medium (CPP-CA 30/20 S/N supplemented with 0.1 mg/L 2,4-D and 0.2 mg/L zeatin) containing either 75 or 100 mg/L kanamycin. Calli growing healthy on the selective media were transferred to fresh selective medium as they appeared. About 285 green kanamycin resistant calli were obtained from about $4.8 \times 10^6$ protoplasts. These calli were transferred to B5-0.1 medium (B5 medium according to Gamborg, O., Miller, R., Ojima K. (1968) *Experimental Cell Research* 50: 151–158 containing 0.1 mg/l 2,4 D) supplemented with 200 mg/L Claforan and 100 mg/L kanamycin to induce embryogenic calli and B5 medium without growth regulators was used to regenerate plants.

Example 9

Transformation of Chicory (Cichorium sp.) with an Auxotrophic Agrobacterium Strain.

Seeds of chicory were surface-sterilized (in sodium hypochlorite 2%) rinsed and germinated on MS20 medium and grown at 27 ° C. for 4 to 8 weeks. Leaf discs of about 4–6 mm diameter were transferred to MSN20 medium [MS salts(Murashige and Skoog, supra), vitamins according to Nitsch and Nitsch 1965, *Ann. Phys. Veg* 7, 251–266), glycin 2,0 mg/L, sucrose 20 g/L pH 5.8, agar 8 g/L) supplemented with 1 mg/L BAP, 0.2 mg/L NAA and 0.01 mM methionine, taking care that the abaxial surface of the leaf discs is in contact with the medium. After 1 day, the leaf discs were submersed for 20 minutes in a bacterial suspension (OD600 between 0.01–0.1) of *Agrobacterium tumefaciens* LBA4404met comprising the T-DNA vector pNUN7. pNUN7 is a plasmid comprising a T-DNA with a CAMV 35S promoter -GUS-intron chimeric gene as described by Van Canneyt et al. (supra) and a chimeric selectable nptII gene. The plasmid further comprises a bacterially expressed kanamycinresistance gene.

The leaf discs are further incubated on MSN20 supplemented with 1 mg/L BAP, 0.2 mg/L NAA for two days and then washed in liquid MS20 medium. The washed leaf discs are further incubated on selective medium MNS20 supplemented with 1 mg/L BAP, 0.2 mg/L NAA and 100 mg/L kanamycin (with transfer to fresh selective medium every 14 days). After about 5 weeks the selection medium is changed to MS20 with 0.1–1 mg/L BAP and 100 mg/L kanamycine.

About 20 kanamycin resistant transformed plants were generated from 48 leaf pieces.

Example 10

Agrobacterium-mediated Transformation of DSM6009 Corn Protoplasts

Corn protoplasts of the genotype DSM6009 are prepared according to EP 0 469273 A1, and co-cultivated for 2–3 days with *Agrobacterium tumefaciens* LBA4404met comprising the helper plasmid pAL4404 and the T-DNA vector pGSV71. pGSV71 is a T-DNA vector derived from pGSC1700 (Cornelissen and Vandewiele, 1989, *Nucl. Acids Res.* 17: 833) differing. by the absence of the -lactamase gene and the presence of the T-DNA characterized by the sequence of SEQ ID No. 1. pGVS71 comprises the selectable chimeric bar marker gene, operably linked to a CaMV35S promoter and the 3' end of the nopaline synthase gene. After 2–3 days, protoplasts are washed with W5-buffer and cultured further according to EP 0 469273 A1. Selection and regeneration of transformed cells into transformed corn plants are as described in EP 0 469273 A1. Phosphinotricin resistant corn plants are obtained and the presence of the transgene is verified by polymerase chain reaction and southern analysis.

Example 11

Isolation and Evaluation of Auxotrophic Agrobacterium Strain ATHVade,his

An Agrobacterium strain auxotrophic for two nutrients was selected by the following protocol, starting from strain ATHV (described by Lazo et al, 1991, *Biotechnology* 9: 963–967 as strain AGL0).

Strain ATHV was grown overnight in LB supplemented with 100 μg/ml rifampin (Rif). One ml of this cell culture was used to inoculate a flask containing 20 ml LB/100 μg Rif, and allowed to grow for 4 hrs (with shaking) at 30° C. Ten ml of this culture was illuminated with 254 nm UV-light for 2 to 4 hr. 100 μl of the UV-illuminated culture was plated on LB/Rif medium solidified with agar, and incubated in the dark at 30° C. for 2 to 3 days. The resulting colonies were replica-plated to minimal medium (M9; see Example 1) and LB medium both supplemented with 100 μg/ml rifampin. Colonies unable to grow on the minimal medium were isolated and analyzed for nutrient requirements. One strain, designated ATHVade,his, was identified which required the addition of adenine for growth, and additionally grew much better when histidine was added (see Table 1). This double requirement for exogenously supplied nutrients allows even better growth control of this Agrobacterium strain.

TABLE 1

Growth of ATHVade,his in minimal medium with different concentrations of adenine (ade) and histidine (his). The values represented are OD600 measured after two days of growth.

| | Ade 0 mM | Ade 0.005 mM | Ade 0.01 mM | Ade 0.05 mM | Ade 0.1 mM |
|---|---|---|---|---|---|
| His 0 mM | 0.019 | 0.059 | 0.067 | 0.111 | 0.129 |
| His 0.01 mM | 0.034 | 0.07 | 0.071 | 0.111 | 0.141 |
| His 0.05 mM | 0.04 | 0.093 | 0.112 | 0.144 | 0.196 |
| His 0.1 mM | 0.035 | 0.102 | 0.123 | 0.163 | 0.221 |

To analyze whether strain ATHVade,his was still c apa ble of T-DNA transfer, a derivative strain containing T-DNA vector pNUN7 (see Example 9) was used to infect leaf discs of *N. tabacum* and *N. sylvestris* in comparison with a wild type ATHV strain containing the same T-DNA vector. In *N. tabacum* about 115 transformed shoots were obtained from about 50 leaf segments after inoculation with ATHV (pNUN7), while about 112 transformed shoots were obtained from about 50 leaf segments after inoculation with ATHVade,his(pNUN7). In *N. sylvestris* about 17 transformed shoots were obtained from about 50 leaf segments after inoculation with ATHV(pNUN7), while about 40 transformed shoots were obtained from about 50 leaf segments after inoculation with ATHVade,his(pNUN7).

Example 12

In Planta Transformation of Petunia (*Petunia hybrida*)

Either internodia or shoot tips (excised below the node bearing the first 3 to 4 mm leaf) were isolated from axenically grown plants and incubated for about 7 to 10 min with Agrobacterium LBA4404metHV(pNUN7) cell suspension, blotted dry and cultured on plant culture media, as described in the previous examples. The shoot tips were not immersed but put with the cut end in a well containing the Agrobacteria. Internal examination of explants and regenerating plants, at different times, revealed GUS expression associated at least with vascular bundles.

The bacterial presence was estimated in the different parts of the plants after 4 weeks culture in vitro. To this end, parts of different leaves were removed, ground in a tube containing 100 μl LB. After settling, 20 μl of the supernatants was plated on LB medium containing rifampin. The results are summarized in Table 2.

TABLE 2

Number of bacteria determined in different infected Petunia plant parts

| Tested leaf | # of bacteria in 20 μl plant extract from nodal cultures (individual exp.) | # of bacteria in 20 μl plant extract from shoot tip cultures (individual exp.) |
|---|---|---|
| Upper tip | 204/92/0 | >200/>500/0 |
| Upper center | 271/0/0 | >500/6/0 |
| Middle tip | >500/5/0/>1000/>500/26/>1000 | 200/1/>200/>1000/>500/>100/0/5/>1000/>1000 |
| Middle center | 10/0/50 | >200/29/500 |
| Basal tip | >500/449/3 | >500/19/>1000 |
| Basal center | >500/0/0 | >2000/>1000/0 |

All plants tested contained Rif resistant Agrobacteria, and about 75% of all the samples tested contained Agrobacteria.

Example 13

Comparison of Transformation Efficiency of A. tumefaciens Strain LBA4404metHV with LBA4404 HV in Transformation of Brassica napus.

The transformation efficiency of A. tumefaciens LBA4404metHV derivatives (containing T-DNA vectors with a chimeric β-glucuronidase gene) in the transformation of embryo's obtained from microspore cultures of Brassica napus "Topas" was compared with the transformation efficiency of LBA4404HV and GV3101 containing similar T-DNA vectors. The sequence of events in the transformation can be summarized as follows:

a. establishing cell cultures from microspores of B. napus
b. generating somatic embryo's
c. co-cultivating those embryo's with a A. tumefaciens strain comprising the T-DNA vectors
d. grow the co-cultivated embryo's to the "hypocotyl" stage and inducing secundary embryogenesis.
e. Submit the secundary embryo's to a selective regime
f. Score the surviving embryo's for β-glucuronidase expression.

When LBA4404metHV comprising a T-DNA vector with a chimeric β-glucuronidase gene was used to transform B. napus embryo's about 80% of the secundary embryo's obtained had GUS+ sectors, whereas only 5% of the secundary embryo's exhibited such spots when co-cultivated with LBA4404HV comprising a similar T-DNA vector. In a more quantitative assay the transformation efficiency of LBA4404metHV, LBA4404HV and GV3101, each comprising a T-DNA vector with a chimeric β-glucuronidase gene was compared. The results, demonstrating a more efficient transformation with LBA4404metHV, are summarized in Table 3.

TABLE 3

Efficiency of transformation, assayed by GUS expression

| Host strain | Percentage embryo's with GUS+ sectors | Average number of GUS+ sectors per embryo |
|---|---|---|
| LBA4404metHV | 82 | >20 |
| LBA4404HV | 67 | 5–10 |
| GV3101 | 59 | ±5 |

---

What is claimed is:

1. A process to produce a dicotyledonous transgenic plant, said plant comprising a foreign DNA fragment integrated into the genome of at least some of its cells, said process comprising the following steps:

1) providing a plant which is systemically infected with an Agrobacterium strain auxotrophic for methionine or cysteine, or adenine and histidine, harboring a DNA of interest which is operably linked to at least one T-DNA border sequence; and 2) generating a transgenic plant from a single cell or a group of cells isolated from said systemically infected plant.

2. The process according to claim 1, wherein said plant which is systemically infected with said auxotrophic Agrobacterium strain is regenerated from explant tissue inoculated with said auxotrophic Agrobacterium strain.

3. The process according to claim 2, wherein said regeneration of said plant which is systemically infected with said auxotrophic Agrobacterium strain is performed on a plant regeneration medium, in the absence of a compound with a bacteriocidal or bacteriostatic effect on said auxotrophic Agrobacterium strain.

4. The process according to claim 1, wherein said transgenic plant is generated by in vitro regeneration of a protoplast isolated from said systemically infected plant.

5. The process according to claim 1, wherein said transgenic plant is generated by in vitro regeneration of an explant tissue isolated from said systemically infected plant.

6. The process according to claim 1, wherein said transgenic plant is generated by in vitro regeneration of a microspore of said systemically infected plant.

7. The process according to claim 1, wherein said transgenic plant is generated by germination of transformed progeny seed of said systemically infected plant.

8. The process according to claim 1, which further comprises the step of applying a nutrient required by said auxotrophic Agrobacterium strain to allow said Agrobacterium to grow on unsupplemented minimal medium to at least part of the systemically infected plant prior to the step of generating a transformed plant.

9. The process according to claim 8, wherein said required nutrient is applied to the infloresence meristem or immature infloresence of said systemically infected plant.

10. The process according to claim 1, wherein said Agrobacterium is LBA4404metHV, deposited as LMG P-18486, or ATHV ade,his, deposited as LMG P-18485.

11. Bacterial strain LBA4404metHV, deposited as LMG P-18486.

12. Bacterial strain ATHV ade,his, deposited as LMG P-18485.

13. A method for producing a transgenic plant, said plant comprising a foreign DNA fragment integrated into the genome of at least some of its cells, said process comprising:

a. cocultivating a plant cell, plant tissue, explant or plant with an Agrobacterium strain auxotrophic for methionine or cysteine, or for adenine and histidine, to generate a transgenic cell; and b. regenerating a transgenic plant from said transgenic cell.

14. The method according to claim 13, wherein said Agrobacterium strain is selected from the group consisting of LBA4404metHV, deposited as LMG P-18486, ATHV ade,his, deposited as LMG P-18485, and derivatives thereof that retain auxotrophy for the same nutrients as those strains.

15. The method according to claim 13, wherein said plant is selected from the group consisting of sweet pepper, cucumber, sunflower, leek, sugar beet, tomato, carrot, *Brassica napus*, chichory, corn, wheat, barley, triticale, oat, rye and rice.

16. The method according to claim 13, wherein said plant cell is a plant protoplast.

17. The method according to claim 16, wherein said protoplast is selected from the group consisting of a carrot petiole protoplast, a sugarbeet guard cell protoplast and a corn protoplast.

18. The method according to claim 13, wherein said plant tissue is an embryogenic callus tissue.

19. The method according to claim 18, wherein said embryogenic callus tissue is a sugarbeet callus or a cucumber callus.

* * * * *